(12) United States Patent
Tyber et al.

(10) Patent No.: US 8,167,949 B2
(45) Date of Patent: May 1, 2012

(54) HYDROSTATIC INTERBODY

(75) Inventors: Jeffrey Tyber, Bethlehem, PA (US);
Charles Wing, Center Valley, PA (US);
Larry Pijanowski, Red Hill, PA (US)

(73) Assignee: Aesculap Implant Systems, LLC,
Center Valley, PA (US)

( * ) Notice: Subject to any disclaimer, the term of this patent is extended or adjusted under 35 U.S.C. 154(b) by 1133 days.

(21) Appl. No.: 12/019,760

(22) Filed: Jan. 25, 2008

(65) Prior Publication Data

US 2009/0192615 A1 Jul. 30, 2009

(51) Int. Cl.
*A61F 2/44* (2006.01)
(52) U.S. Cl. .................................... 623/17.16
(58) Field of Classification Search ......... 623/17.11–16, 623/17.15
See application file for complete search history.

(56) References Cited

U.S. PATENT DOCUMENTS

| 4,904,261 | A | 2/1990 | Dove et al. |
| 5,827,328 | A | 10/1998 | Buttermann |
| 6,660,038 | B2 * | 12/2003 | Boyer et al. ............... 623/17.15 |
| 6,758,863 | B2 | 7/2004 | Estes et al. |
| 6,984,234 | B2 | 1/2006 | Bray |
| 7,232,464 | B2 | 6/2007 | Mathieu et al. |
| 2005/0125063 | A1 | 6/2005 | Matge |
| 2006/0020342 | A1 * | 1/2006 | Ferree et al. ............... 623/17.15 |
| 2006/0030851 | A1 | 2/2006 | Bray |
| 2007/0093901 | A1 * | 4/2007 | Grotz et al. ............... 623/17.11 |
| 2009/0210064 | A1 | 8/2009 | Lechmann et al. |

FOREIGN PATENT DOCUMENTS

| WO | WO 2006/037621 A1 | 4/2006 |
| WO | WO 2006/108114 A2 | 10/2006 |
| WO | WO 2007/115208 A2 | 10/2007 |

OTHER PUBLICATIONS

Non-Final Office Action Dated Feb. 16, 2011, for U.S. Appl. No. 12/256,713.

* cited by examiner

*Primary Examiner* — Thomas C. Barrett
*Assistant Examiner* — David Bates
(74) *Attorney, Agent, or Firm* — RatnerPrestia

(57) ABSTRACT

An intervertebral implant includes an upper surface configured for engagement with a first vertebral body, and a lower surface configured for engagement with a second vertebral body. A wall extends between the upper surface and the lower surface, and forms a chamber for containing osteogenic material. At least a portion of the wall is collapsible from a first position associated with a first volume of the chamber to a second position associated with a second volume of the chamber. The second volume is less than the first volume.

5 Claims, 10 Drawing Sheets

US 8,167,949 B2

HYDROSTATIC INTERBODY

FIELD OF THE INVENTION

The present invention relates generally to implants for placement into bone recesses, and more specifically to interbodies for dynamically transmitting loads while promoting fusion between bones.

BACKGROUND OF THE INVENTION

In spinal fusion, two or more vertebrae are joined by additional bone material placed between the vertebrae. Once fusion is complete, the bone material immobilizes the vertebrae. Spinal fusion is used primarily to treat pain caused by abnormal motion of the vertebrae. Anterior lumbar interbody fusion (ALIF) is a spinal fusion technique that can be used for treating degenerative discs from an anterior approach. The anterior approach allows access to the interbody space with minimal damage to the posterior musculature, while allowing full decompression of the diseased disc. During an ALIF procedure, an interbody device is inserted within the intervertebral body space. This interbody is generally composed of PEEK or titanium with a central opening for bone graft material, which is typically an autograft or allograft material. The objective of interbody fusion is to fuse the central graft material to the cranial and caudal endplates, creating a rigid boney union between motion segments.

Known interbody designs have a propensity to stress-shield the graft material. That is, the interbodies, or the fasteners used to anchor the interbodies, absorb axial loads during settling of the implant. This has the effect of shielding the graft material from axial loads. Some interbody designs are configured to expand in an axial direction after being implanted to increase the height of the disc space to a desired spacing. This also stress-shields the graft material, and actually removes load from the graft material because the height of graft space expands.

SUMMARY OF THE INVENTION

In a first exemplary embodiment of the invention, an intervertebral implant includes an upper surface configured for engagement with a first vertebral body, and a lower surface configured for engagement with a second vertebral body. A wall extends between the upper surface and the lower surface. A chamber, which is enclosed within the wall, includes an upper end opening through the upper surface, and a lower end opening through the lower surface. The wall includes a collapsible section between the upper surface and the lower surface. The collapsible section is collapsible from a first position associated with a first volume of the chamber to a second position associated with a second volume of the chamber. The second volume is less than the first volume.

In a second exemplary embodiment of the invention, an intervertebral implant includes an upper plate configured for engagement with a first vertebral body, and a lower plate configured for engagement with a second vertebral body. A chamber extends between the upper plate and the lower plate. The chamber contains an osteogenic material under a hydrostatic pressure in the chamber. The upper plate is axially movable toward the lower plate to reduce the volume of the chamber and increase the hydrostatic pressure on the osteogenic material in the chamber.

In a third exemplary embodiment of the invention, an intervertebral implant includes a body formed of a shape memory material. The body is deformable in response to temperature from a pre-insertion configuration to a post-insertion configuration. In addition, the body forms a chamber and contains an osteogenic material in the chamber. The chamber has a first volume and exerts a first hydrostatic pressure on the osteogenic material in the pre-insertion configuration. The chamber has a second volume and exerts a second hydrostatic pressure on the osteogenic material in the post-insertion configuration. The second volume is less than the first volume, and the second hydrostatic pressure is greater than the first hydrostatic pressure.

BRIEF DESCRIPTION OF THE DRAWINGS

The following description will be more clearly understood in conjunction with the drawing figures, of which.

DETAILED DESCRIPTION OF THE PREFERRED EMBODIMENTS

Figure 1:
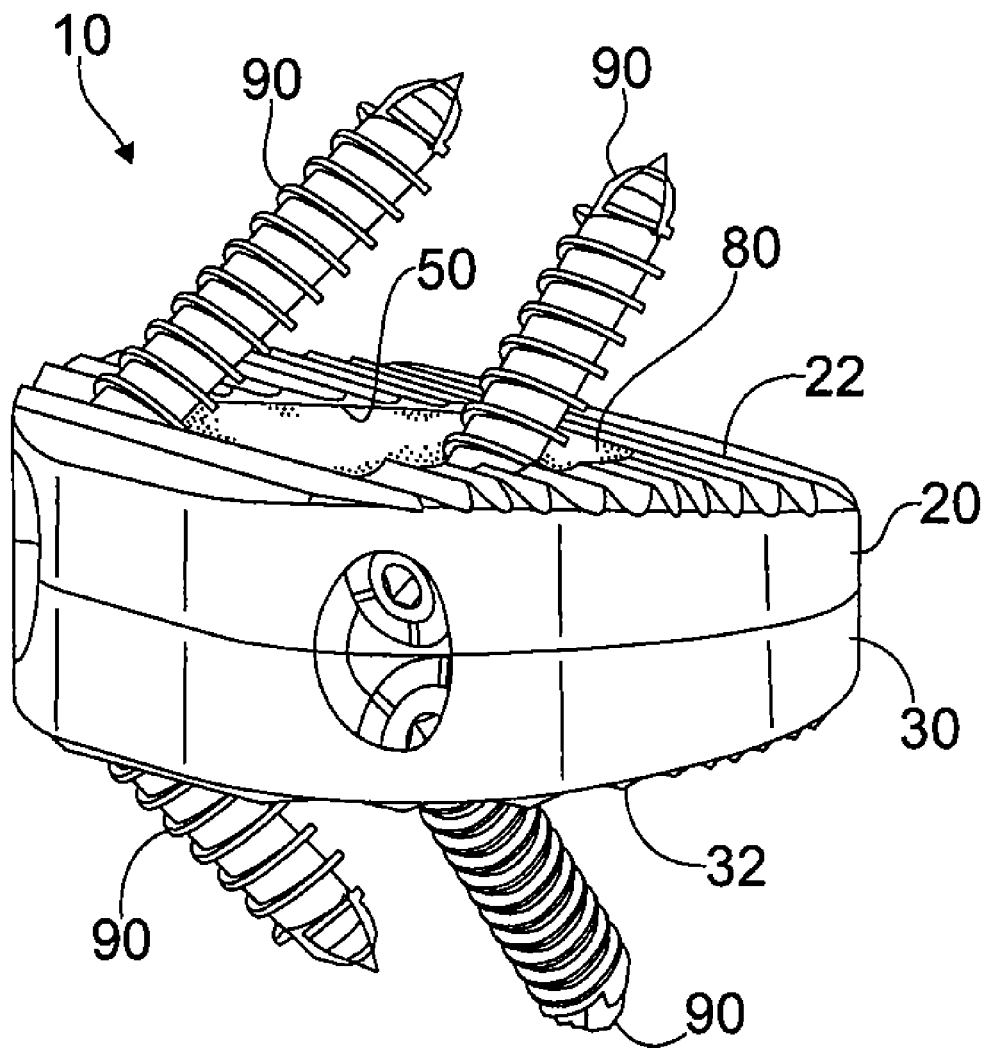
FIG. 1 is a perspective view of a first exemplary embodiment of an interbody in accordance with the present invention.

Although the invention is illustrated and described herein with reference to specific embodiments, the invention is not intended to be limited to the details shown. Rather, various modifications may be made in the details within the scope and range of equivalents of the claims and without departing from the invention.

Interbody implants in accordance with preferred embodiments of the invention address a number of interests. One interest is to provide a rigid structure that maintains proper spacing between vertebrae. A second interest is to minimize the pre-implantation height of the interbody, so that the interbody can fit into compressed disc spaces. A third interest is to provide an interbody that provides sufficient space for graft material and promotes fusion of that graft material. Applicants have observed that these three interests frequently compete with one another. Moreover, Applicants have observed that known interbodies fail to balance and satisfy all three interests. Many known interbodies appear to disregard the third interest, namely the interest of promoting fusion of graft material in the implant. This interest is commonly sacrificed in favor of the one of the other competing interests.

To promote fusion of the graft material within the interbody, the interbody should allow some load to be maintained on the graft material. A consistent loading on the graft material is important during the fusion process to encourage bone growth in the bone tissue. The importance of maintaining load on graft material is rooted in Wolff's Law. Under Wolff's Law, healthy bone will adapt to loads it is placed under, and will remodel itself to become stronger if the loading increases. Conversely, if the loading on a bone is decreased or removed, the bone will gradually become weaker. That is, there is no stimulus for continued remodeling of the bone to maintain bone mass. In the context of spinal fusion, Wolff's Law holds that applying consistent loading to the graft material promotes fusion.

To balance the competing interests described above, the embodiments of the present invention provide structures that dynamically transmit axial load to the graft material during interbody subsidence, while providing a rigid structure to maintain proper disc space height. During subsidence, the bone graft material is confined within the chamber and is compressed under load. As a result, hydrostatic pressure develops in the bone graft material, with pressure bearing on the material from multiple directions, including the axial and radial directions.

The preferred interbodies in accordance with the invention include a central chamber filled with osteogenic material. For purposes of this description, "osteogenic material" includes but is not limited to any material that promotes bone growth or healing, including autograft or allograft material, or synthetic graft material. The osteogenic material is maintained under compression to form a solid fusion between the adjacent vertebral bodies.

In contrast to interbodies that are designed strictly to expand after insertion into the disk space, preferred interbodies in accordance with the invention include a contraction mechanism that allows the interbodies to contract under load over time, reducing the volume of the chamber containing the osteogenic material. Decreasing the size of the interbody over time promotes fusion of the osteogenic material by applying a constant pressure on the material. The chamber radially encloses the osteogenic material, so that the osteogenic material has no room to expand or migrate during an axial contraction of the interbody. This has the effect of applying a constant pressure both axially and radially around the osteogenic material. Constant application of pressure, or a gradual increase in pressure as the case may be, promotes fusion of the osteogenic material under Wolff's Law. Because the embodiments of the invention maintain or increase hydrostatic pressure on the osteogenic material, fusion of the bone material is promoted.

Contraction mechanisms in accordance with the invention may take one of several forms that allow the interbodies to collapse or shrink with respect to one or more planes of reference. The contraction mechanisms are designed to contract in response to changes in loading on the spine, subsidence of the interbody into the end plates of the vertebrae, resorbing of the osteogenic material, or changes in temperature. As a graft material resorbs into the body, for example, the volume of the material may decrease and no longer be under hydrostatic pressure in the chamber. In such cases, the contraction mechanism allows the interbody to collapse by a controlled amount to reduce the volume of the graft space and maintain constant compression on the graft material. The contraction mechanism can be designed to maintain equilibrium between the osteogenic material's resistance to compression, and the loads bearing on the interbody.

Figure 2:
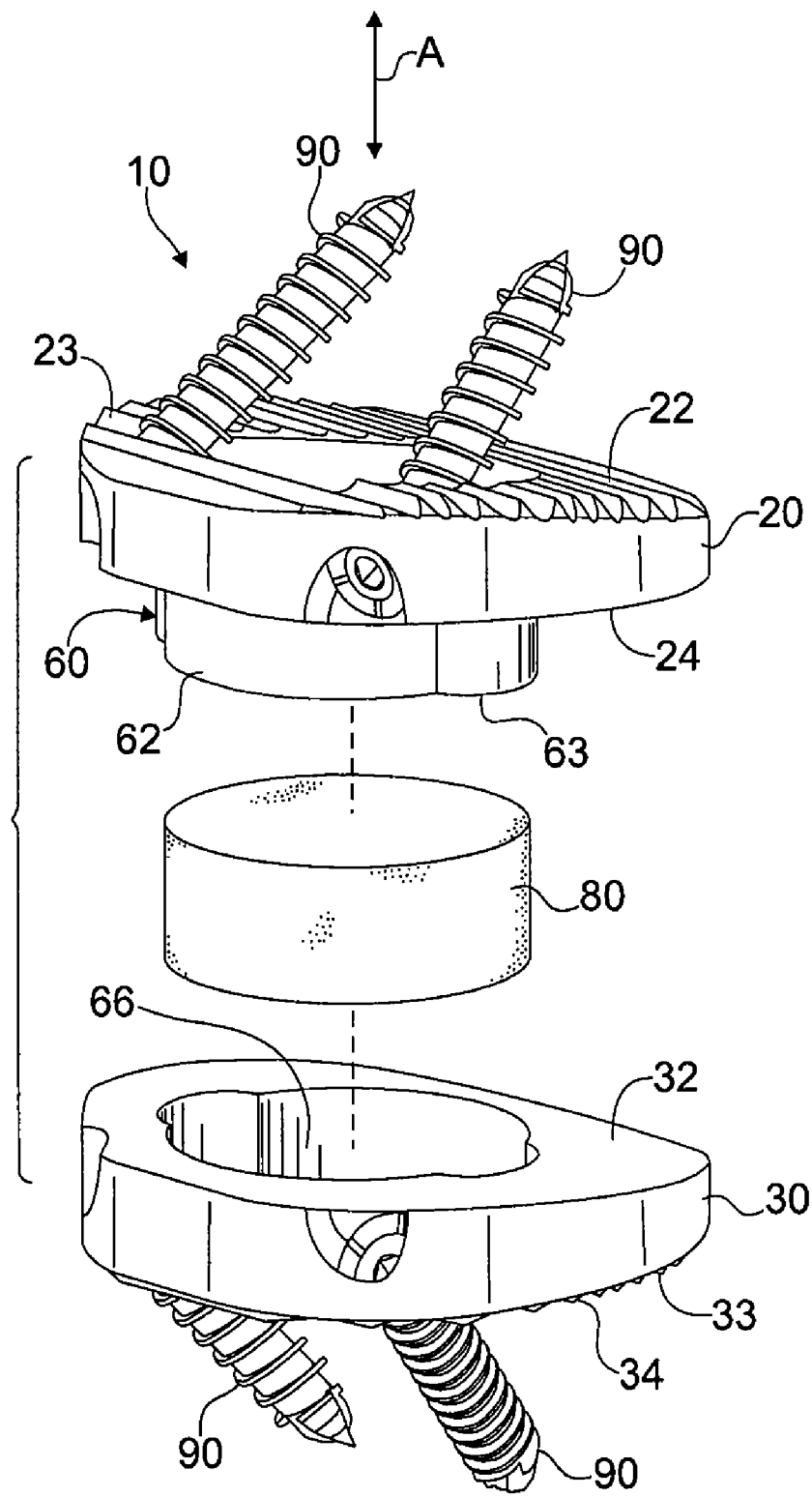
FIG. 2 is an exploded perspective view of the interbody shown in FIG. 1.

Referring now to FIGS. 1 and 2, an implant 10 in accordance with a first exemplary embodiment of the invention is shown. Implant 10 includes an upper plate 20 and a lower plate 30. Upper plate 20 has an upper surface 22 forming an exterior surface on the implant, and a lower surface 24 forming an interior surface of the implant. Similarly, lower plate 30 has a lower surface 34 forming an exterior surface on the implant, and an upper surface 32 forming an interior surface of the implant. Upper and lower plates 20 and 30 both have ring-shaped bodies that surround hollow interiors. When upper and lower plates 20 and 30 are joined or stacked relative to one another, the hollow interiors align to form a central chamber 50 for containment of an osteogenic material 80. The superior and inferior end plates adjacent implant 10 form the upper and lower walls of chamber 50.

As noted above, implants in accordance with the present invention include a contraction mechanism that facilitates a controlled rate of implant collapse. Contraction may occur solely in the "axial" direction, represented by axis "A" in FIG. 2, the "radial" direction, which is any direction perpendicular to axis "A", or a contraction on both the axial and radial directions. Implant 10 includes a telescoping contraction mechanism 60 that permits upper plate 20 to collapse axially toward lower plate 30. A plug or shaft 62 extends from lower surface 24 of upper plate 20. Lower plate 30 includes a socket 66 that receives the shaft 62 during contraction of implant 10. Shaft 62 is generally cylindrical and forms a bore 63. Bore 63 and socket 66 collectively form part of chamber 50 for containing osteogenic material 80.

Figure 3:
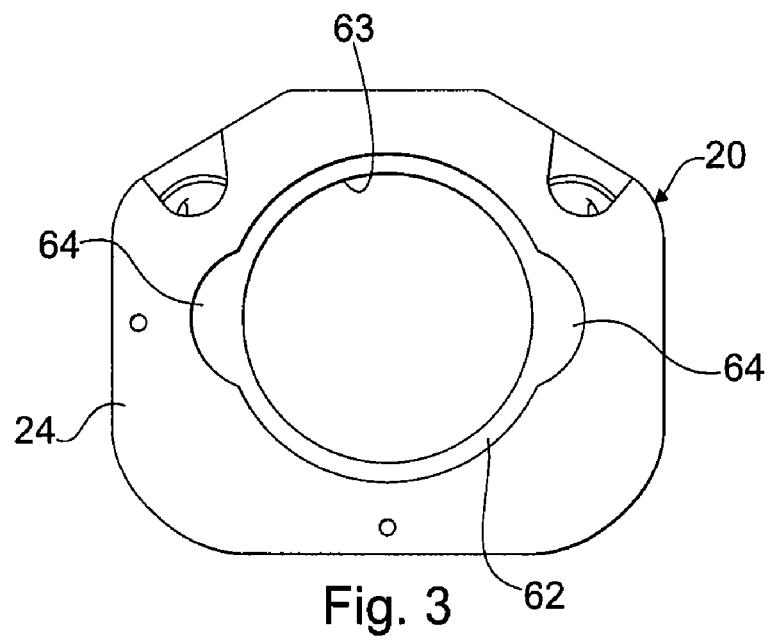
FIG. 3 is a bottom view of a superior component of the interbody shown in FIG. 1.
Figure 4:
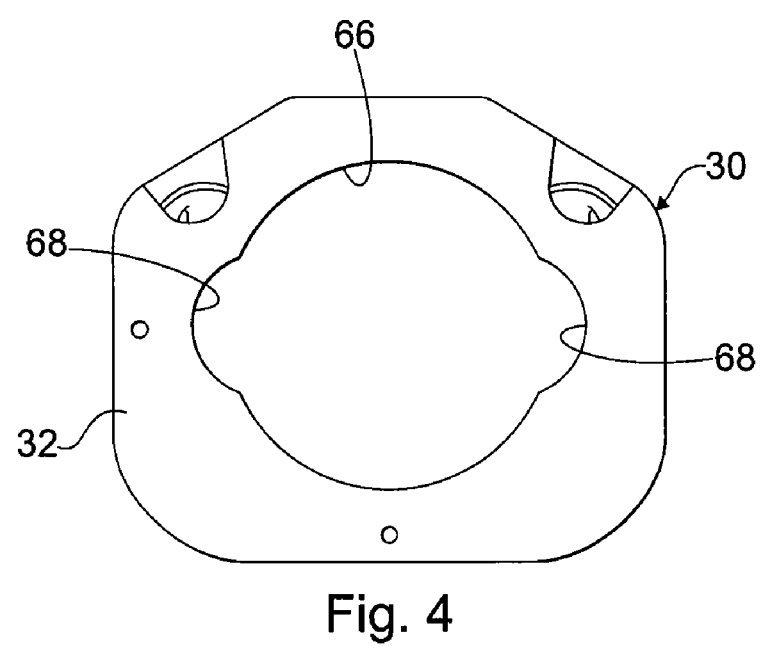
FIG. 4 is a top view of an inferior component of the interbody shown in FIG. 1.

Shaft 62 is configured to slide telescopically into socket 66 during contraction of implant 10. As upper and lower plates 20 and 30 collapse into one another, the volume in chamber 50 decreases. In this arrangement, contraction mechanism 60 is operable to reduce the volume of chamber 50 over time and maintain compression on osteogenic material 80. In the preferred embodiment, implant 10 includes a mechanism for limiting relative rotation between upper and lower plates 20 and 30. Referring to FIGS. 2 and 3, for example, shaft 62 includes a pair of lobes 64. Lobes 64 mate with a pair of diametrically opposed notches 68 in socket 66, shown in FIGS. 2 and 4. Notches 68 telescopically receive lobes 64 as shaft 62 enters the socket 66. The sliding engagement between lobes 64 and notches 68 maintains radial alignment between upper and lower plates 20 and 30, and substantially prevents rotation of one plate relative to the other to stabilize implant 10.

Interbodies in accordance with the invention preferably include surfacing to promote engagement with end plates of vertebral bodies. Referring to FIG. 2, for example, upper plate 20 includes a plurality of ridges 23 and lower plate 30 includes a similar plurality of ridges 33. Upper and lower plates 20, 30 are anchored into adjacent vertebrae with a plurality of bone screws 90. It will be understood, however, that a number of fastener types may be used to anchor the plates, including a variety of screw sizes and configurations.

Figure 5:
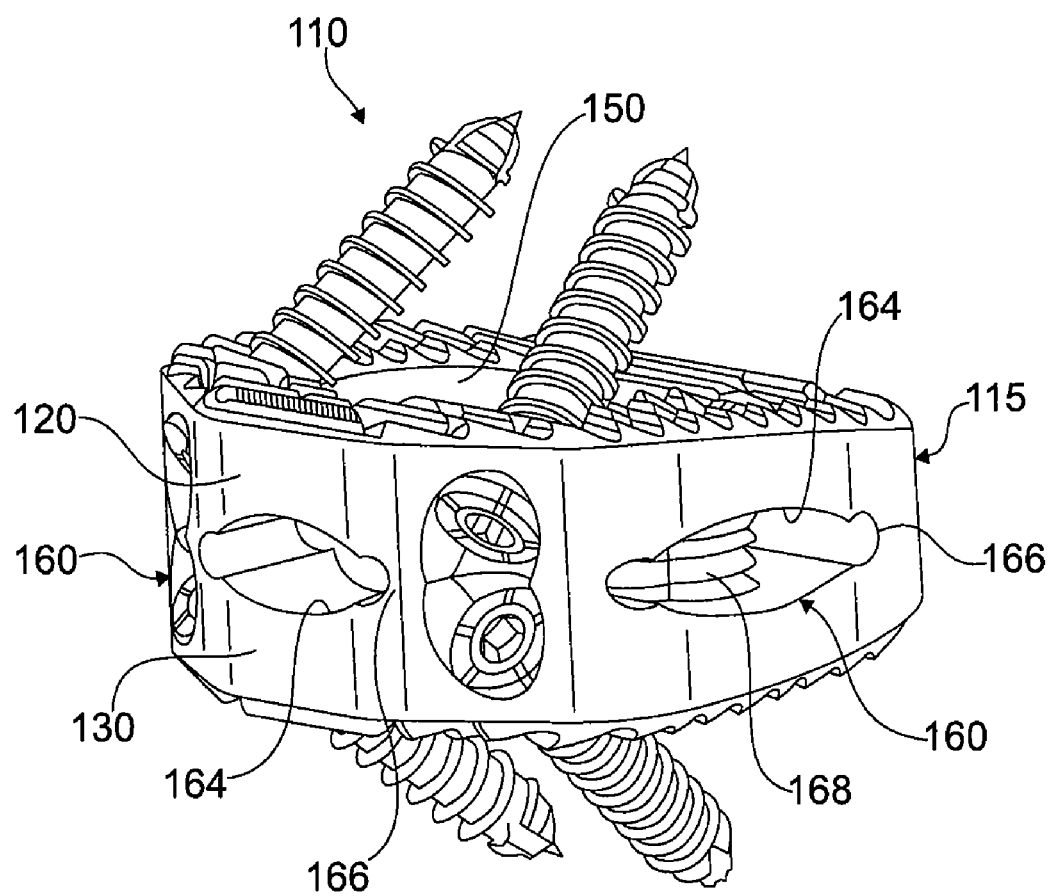
FIG. 5 is a perspective view of a second exemplary embodiment of an interbody in accordance with the present invention.
Figure 6:
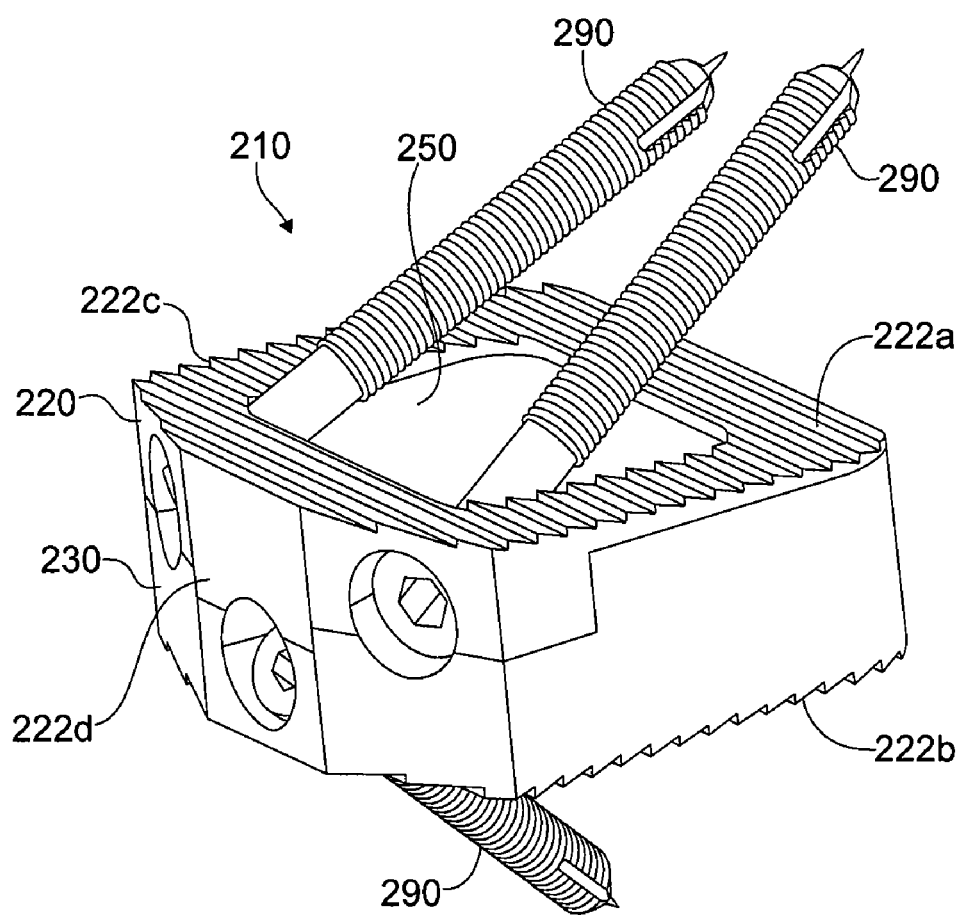
FIG. 6 is a perspective view of a third exemplary embodiment of an interbody in accordance with the present invention.
Figure 7:
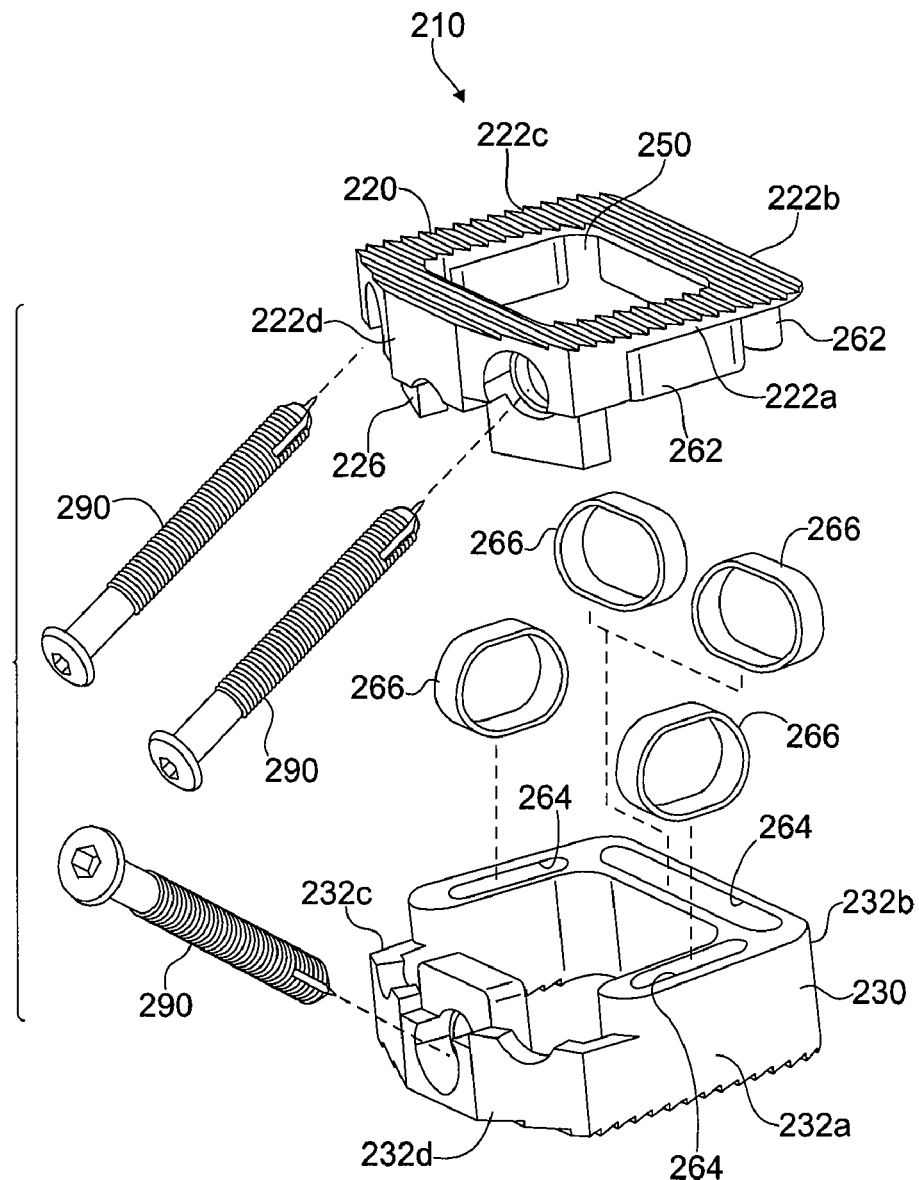
FIG. 7 is an exploded perspective view of the interbody shown in FIG. 6.

Referring now to FIG. 5, an interbody 110 is shown in accordance with an alternative embodiment of the invention. Interbody 110 includes a one-piece body 115 having an upper plate section 120 conjoined with a lower plate section 130.

Body 115 forms a central chamber 150 for containing an osteogenic material. Contraction mechanisms 160 are provided in the walls of body 115 to allow upper plate 120 and lower plate 130 to be collapsible in an axial direction relative to one another. Each contraction mechanism 160 includes a wall section with a large aperture 164 and an elastic member 168 contained in the aperture. Apertures 164 form thinned sections in upper and lower plates 120 and 130 that deflect in response to axial load. In this configuration, upper and lower plates 120, 130 are permitted to collapse axially relative to one another when subject to axial loads. Elastic members 168 provide limited resistance to contraction and absorb some of the axial load. Apertures 164 are separated from adjacent fastener holes or other apertures by hinge portions 166 that allow the plates 120, 130 to collapse.

Elastic members 168 provide a further benefit by absorbing some of the compressive load and protecting against end plate failure. That is, each elastic member 168 counteracts the compressive force and reduces the total net force on the osteogenic material and reaction force on the end plates. Elastic members 168 further allow interbody 110 to self-distract after insertion into the disc space. Distraction may occur by mechanical expansion of the elastic members, or by thermal expansion in the case where the elastic members are formed of shape memory materials.

Referring now to FIGS. 6-8B, an interbody 210 is shown in accordance with another alternative embodiment of the invention. Interbody 210 includes an upper plate 220 telescopically received in a lower plate 230. Upper and lower plates 220, 230 form generally rectangular ring bodies with open center areas that collectively form a chamber 250 for osteogenic material. Interbody 210 further includes contraction mechanisms 260 in the upper and lower plates 220, 230. Lower plate 230 has three hollow sidewalls 232a, 232b, 232c, each having a hollow socket 264 with one or more oval-shaped spring members 266 in each socket. A fourth sidewall 232d, which represents the anterior side of interbody 210 after insertion, forms a large tab 236. Upper plate 220 has three sidewalls 222a, 222b, 222c with plug extensions 262. A fourth sidewall 222d has a recess 226 that receives tab 236 of lower plate 230. Plug extensions 262 of sidewalls 222a, 222b, 222c are telescopically received in sidewalls 232a, 232b, 232c, respectively. In this arrangement, upper and lower plates 220, 230 are permitted to collapse in an axial direction relative to one another. Spring members 266 provide a limited amount of resistance to axial compression so that osteogenic material 280 in chamber 250 may be shielded from some of the axial load during collapse.

Figure 8A:
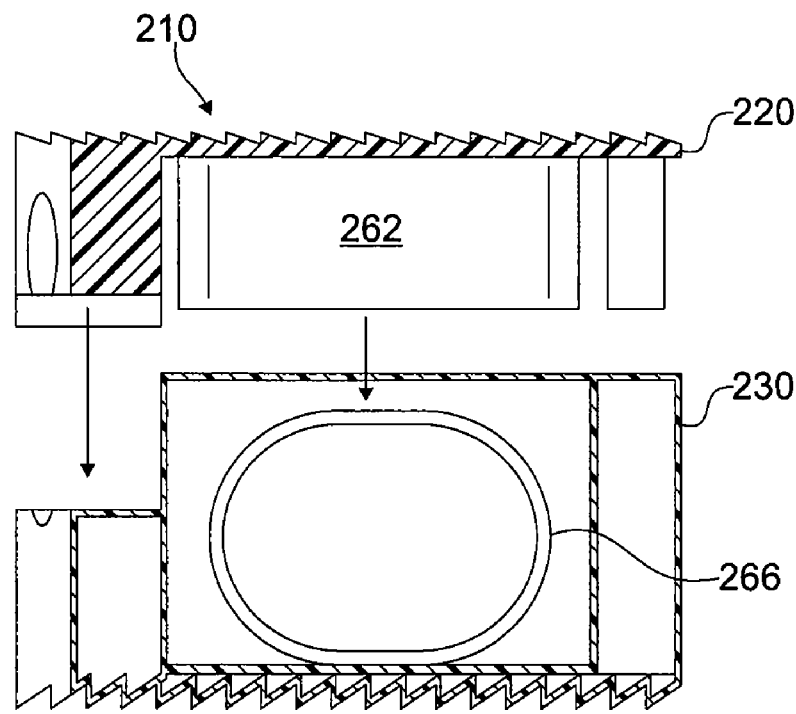
FIG. 8A is an exploded side view of the interbody of FIG. 6 with a portion cut away to expose an interior component in a first condition.
Figure 8B:
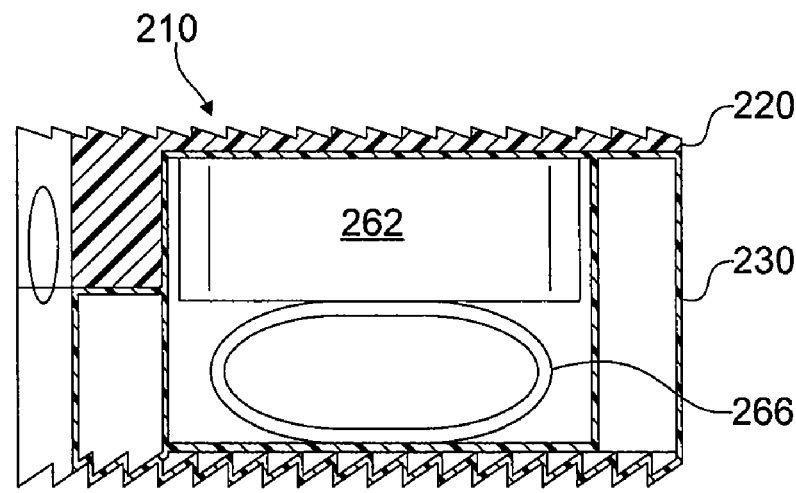
FIG. 8B is an assembled side view of the interbody of FIG. 6 with a portion cut away to expose an interior component in a second condition.

Interbody 210 is configured to be compressed to a thin profile as shown in FIG. 8B to permit the interbody to be inserted into the disc space. After interbody 210 is inserted into the disc space, the interbody is configured to expand or self-distract. Interbody 210 can be compressed by applying axial pressure on upper plate 220 to advance the upper plate into lower plate 230 and compress elastic members 266. To facilitate compression, elastic members 266 may be formed of shape memory material that is inserted into the disc space at a reduced temperature, and subsequently heated to expand the implant. Elastic members 266 may be expanded in response to body temperature or external heat applied to the elastic members. Interbody 210 self-distracts as elastic members 266 expand. After elastic members 266 are fully expanded, they remain flexible to adjust to changes in load on the interbody. As axial load increases, elastic members 266 flex under load, allowing upper plate 220 to collapse into lower plate. Elastic members 266 absorb some of the load, while allowing some of the load to be applied to osteogenic material in chamber 250. The height of chamber 250 decreases by an amount corresponding to the amount of collapse. The interior walls of lower plate 230 remain stationary, so that the volume of chamber 250 decreases as upper plate 220 collapses into lower plate 230. The stationary walls of lower plate 230 confine the osteogenic material and prevent lateral displacement of the material. In this arrangement, collapse of the upper plate 220 into lower plate 230 increases hydrostatic pressure in the graft chamber. The geometry and material of elastic members 266 may be selected to permit a desired range of collapse and increase in hydrostatic pressure.

Figure 9:
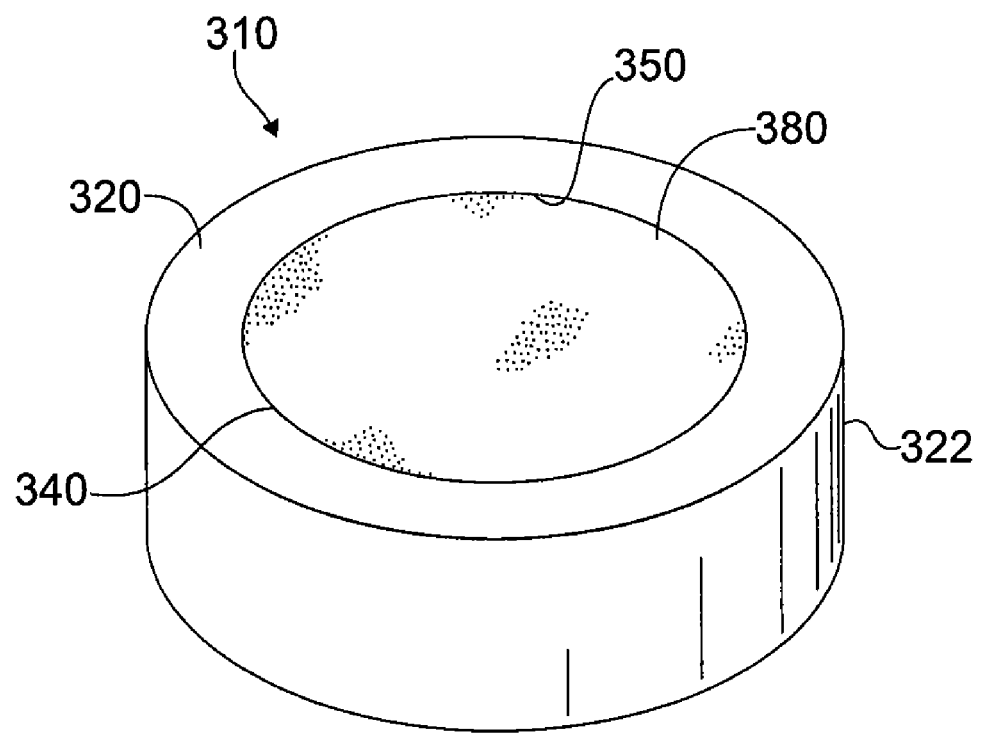
FIG. 9 is a perspective view of a fourth exemplary embodiment of an interbody with biologic material in accordance with the present invention.

Referring now FIG. 9, another exemplary interbody 310 is shown in accordance with the present invention. Interbody 310 includes an annular body 320 that forms an inner wall 340 surrounding a central chamber 350. Chamber 350 contains an osteogenic material 380. Interbody 310 further includes a contraction mechanism provided by a shape memory polymer 322 in annular body 320. Shape memory polymer 322 is designed to contract over time to create hydrostatic pressure in the chamber 350. Annular body 320 may be formed to contract strictly in response to time, the transfer of heat, or both.

Figure 10A:
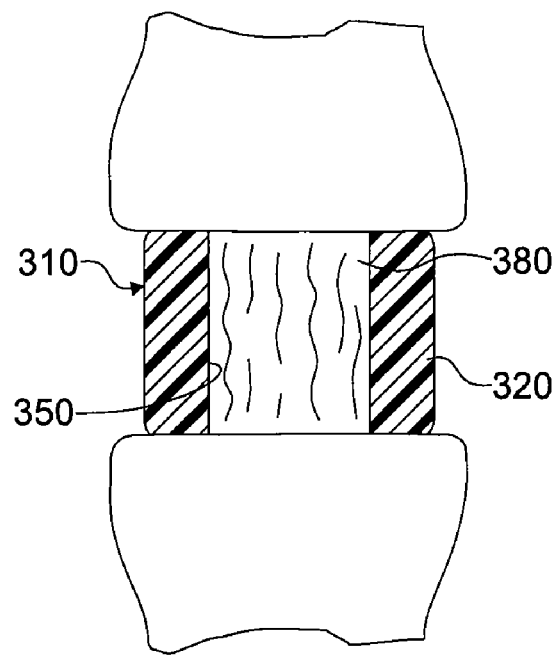
FIG. 10A is a schematic cross-sectional view of the interbody of FIG. 6, shown in a first condition.
Figure 10B:
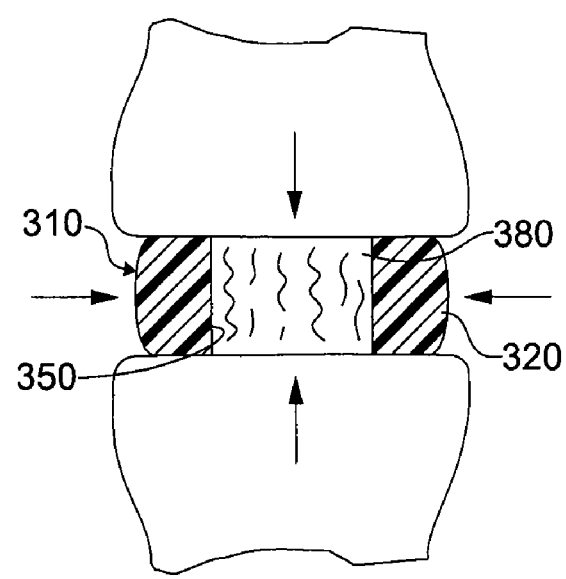
FIG. 10B is a schematic cross-sectional view of the interbody of FIG. 6, shown in a second condition.

Annular body 320 may be designed to contract in the axial direction, radial direction, or a combination of both directions to apply and maintain hydrostatic pressure to osteogenic material 380 in chamber 350. Referring now FIGS. 10A and 10B, interbody 310 is configured to contract in both the axial and radial directions over time. FIG. 10A shows interbody 310 in an intraoperative state, and FIG. 10B shows the same interbody in a post-settling state. Interbody 310 contracts both axially and radially during settling, decreasing the volume of chamber 350. Osteogenic material 380 is confined between the adjoining vertebral bodies and within annular body 320. As a result, hydrostatic pressure in chamber 350 increases in response to contraction of interbody 310.

Figure 11A:
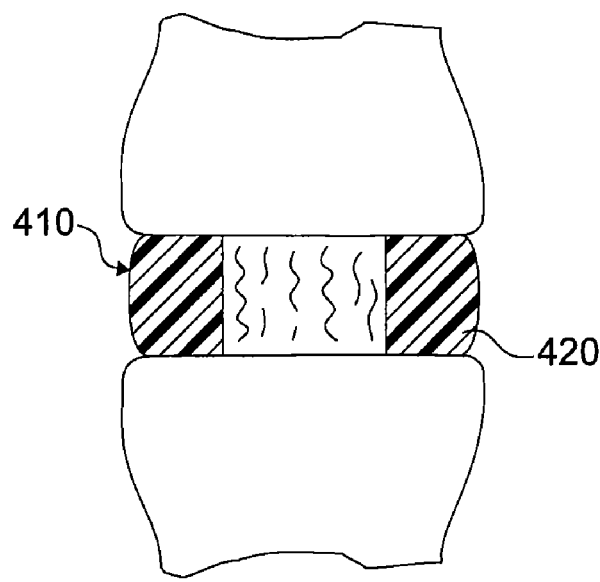
FIG. 11A is a schematic cross-sectional view of a fifth exemplary embodiment of an interbody in accordance with the present invention, shown in a first condition.
Figure 11B:
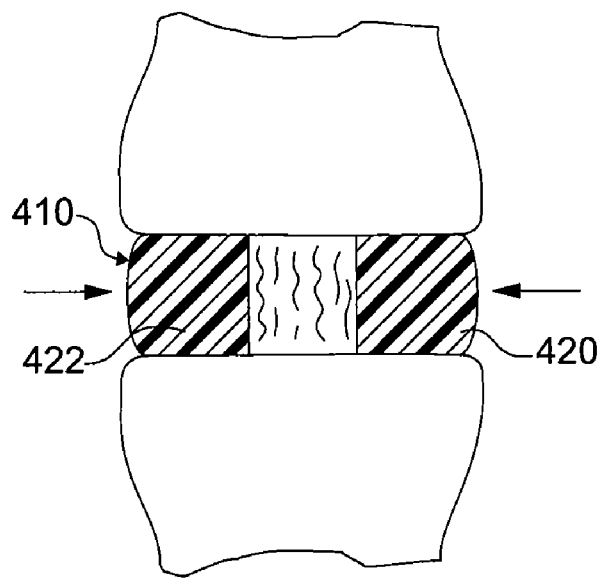
FIG. 11B is a schematic cross-sectional view of a fifth exemplary embodiment of an interbody in accordance with the present invention, shown in a second condition.

In some circumstances, it may be desirable to provide an interbody that contracts only in the radial direction to apply hydrostatic pressure in the radial direction. Referring now FIGS. 11A and 11B, another exemplary interbody 410 is shown in accordance with the present invention that contracts only in the radial direction. Interbody 410 includes an annular body 420 containing a shape memory polymer 422.

Although the embodiments described above are discussed with specific examples of contraction mechanisms, including elastic members and shape memory polymers, a number of materials may be used to allow the interbody to change from a desired pre-implantation configuration to a post-implantation configuration. As noted above, the interbody may include a shape memory material, such as a shape memory metal, ceramic or polymer, that is inserted into a disc space or other bone recess in a pre-implantation shape, and then activated into a post-implantation shape. A number of shape memory materials, many of which may be used in accordance with the present invention, are described in International Pub. No. WO 2006/108114, the contents of which is incorporated by reference in its entirety. Interbodies in accordance with the present invention may also include elastomers, mechanical spring members or any other materials that can deform to a desired post-implantation shape.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. An intervertebral implant comprising an upper plate having an upper surface configured for engagement with a first vertebral body, a lower plate having a lower surface configured for engagement with a second vertebral body, and a chamber between the upper plate and the lower plate, the chamber surrounded by a fixed inner wall in the upper plate and a fixed inner wall in the lower plate, the upper plate forming a first passage extending through the upper surface to facilitate insertion of a first bone screw through the wall and the upper surface into a first vertebral body, the lower plate forming a second passage extending through the lower surface to facilitate insertion of a second bone screw through the wall and the lower surface into a second vertebral body, the upper plate axially movable toward the lower plate to reduce the volume of the chamber and increase the hydrostatic pressure on an osteogenic material in the chamber, the upper plate comprising a hollow plug having a lobe extending outwardly from the plug, and the lower plate comprising a socket having a notch, the socket adapted to telescopically receive the plug when the lobe is radially aligned with the notch to maintain radial alignment between the upper plate and lower plate and substantially prevent rotation of the upper plate relative to the lower plate.

2. The intervertebral implant of claim 1, wherein one of the fixed inner walls comprises a contraction member.

3. An intervertebral implant comprising an upper plate having an upper surface configured for engagement with a first vertebral body, a lower plate having a lower surface configured for engagement with a second vertebral body, a chamber between the upper plate and the lower plate, and an osteogenic material under a hydrostatic pressure in the chamber, the upper plate forming a first passage extending through the upper surface to facilitate insertion of a first bone screw through the upper plate and the upper surface into a first vertebral body, the lower plate forming a second passage extending through the lower surface to facilitate insertion of a second bone screw through the lower plate and the lower surface into a second vertebral body, the upper plate axially movable toward the lower plate to reduce the volume of the chamber and increase the hydrostatic pressure on the osteogenic material in the chamber, the upper plate comprising a hollow plug having a lobe extending outwardly from the plug, and the lower plate comprising a socket having a notch, the socket adapted to telescopically receive the plug when the lobe is radially aligned with the notch to maintain radial alignment between the upper plate and lower plate and substantially prevent rotation of the upper plate relative to the lower plate.

4. The intervertebral implant of claim 1, wherein the lobe is one of a pair of diametrically opposed lobes extending outwardly from the plug, and the notch is one of a pair of diametrically opposed notches formed in the socket, the socket adapted to telescopically receive the plug when the lobes are radially aligned with the notches to maintain radial alignment between the upper plate and lower plate and substantially prevent rotation of the upper plate relative to the lower plate.

5. The intervertebral implant of claim 3, wherein the lobe is one of a pair of diametrically opposed lobes extending outwardly from the plug, and the notch is one of a pair of diametrically opposed notches formed in the socket, the socket adapted to telescopically receive the plug when the lobes are radially aligned with the notches to maintain radial alignment between the upper plate and lower plate and substantially prevent rotation of the upper plate relative to the lower plate.

* * * * *